(12) United States Patent
Sapin

(10) Patent No.: US 12,274,913 B2
(45) Date of Patent: Apr. 15, 2025

(54) REHABILITATION DEVICE AND APPARATUS

(71) Applicant: AXINESIS, Wavre (BE)

(72) Inventor: Julien Sapin, Hannut (BE)

(73) Assignee: AXINESIS, Wavre (BE)

( * ) Notice: Subject to any disclaimer, the term of this patent is extended or adjusted under 35 U.S.C. 154(b) by 60 days.

(21) Appl. No.: 18/019,184

(22) PCT Filed: Aug. 5, 2021

(86) PCT No.: PCT/EP2021/071926
§ 371 (c)(1),
(2) Date: Feb. 1, 2023

(87) PCT Pub. No.: WO2022/029257
PCT Pub. Date: Feb. 10, 2022

(65) Prior Publication Data
US 2024/0252884 A1    Aug. 1, 2024

(30) Foreign Application Priority Data
Aug. 7, 2020   (EP) ..................................... 20190084

(51) Int. Cl.
*A63B 23/12* (2006.01)
*A63B 24/00* (2006.01)
(Continued)

(52) U.S. Cl.
CPC .......... *A63B 23/12* (2013.01); *A63B 24/0062* (2013.01); *A63B 71/0622* (2013.01);
(Continued)

(58) Field of Classification Search
CPC . A63B 23/12; A63B 24/0062; A63B 71/0622; A63B 2024/0012;
(Continued)

(56) References Cited

U.S. PATENT DOCUMENTS 10,720,082 B1    7/2020  Hutabarat et al.
2008/0058045 A1*  3/2008  Cortenraad ......... A63F 3/00643
                                                                463/9
(Continued)

FOREIGN PATENT DOCUMENTS

CA    2844651 A1 *  2/2013  ........... A61B 5/0002
EP    1 583 028        10/2005
(Continued)

OTHER PUBLICATIONS

International Search Report for PCT/EP2021/071926, mailed Nov. 25, 2021, 6 pages.
(Continued)

*Primary Examiner* — Tuyen K Vo
(74) *Attorney, Agent, or Firm* — NIXON & VANDERHYE

(57) ABSTRACT

Disclosed is a device for assessing and/or rehabilitating the upper limbs of a subject including a display surface, a
(Continued)

detection surface, and a processing unit. Also disclosed is a system and an apparatus including the device, and computer-implemented methods using the device.

20 Claims, 9 Drawing Sheets

(51) Int. Cl.
*A63B 71/06* (2006.01)
*G16H 20/30* (2018.01)

(52) U.S. Cl.
CPC ...... *G16H 20/30* (2018.01); *A63B 2024/0012* (2013.01); *A63B 2024/0068* (2013.01); *A63B 2024/0096* (2013.01); *A63B 2071/0625* (2013.01); *A63B 2071/0658* (2013.01); *A63B 2220/805* (2013.01); *A63B 2220/833* (2013.01)

(58) Field of Classification Search
CPC .... A63B 2024/0068; A63B 2024/0096; A63B 2071/0625; A63B 2071/0658; A63B 2220/805; A63B 2220/833; A63B 23/03508; A63B 24/0006; A63B 2220/10; A63B 2220/13; A63B 21/00178; A63B 23/03516; A63B 24/0021; G16H 20/30; A63F 2003/00662; A63F 2003/0088; A63F 2009/2486; A63F 3/00643; A63F 3/00697; A61H 2201/1261
See application file for complete search history.

(56) References Cited

U.S. PATENT DOCUMENTS

| | | | |
|---|---|---|---|
| 2010/0066016 A1* | 3/2010 | Van De Wijdeven | G06F 3/0421 273/237 |
| 2011/0313331 A1* | 12/2011 | Dehez | A61H 1/0285 601/33 |
| 2012/0077163 A1* | 3/2012 | Sucar Succar | A63B 23/16 434/247 |
| 2013/0143718 A1* | 6/2013 | Pani | A63B 21/4035 482/8 |
| 2020/0363887 A1* | 11/2020 | Lipman | G06F 3/0421 |
| 2021/0209327 A1* | 7/2021 | Wu | G02F 1/13338 |

FOREIGN PATENT DOCUMENTS

| | | | |
|---|---|---|---|
| JP | 2017-217277 | 12/2017 | |
| TW | 200816974 | 4/2008 | |
| WO | WO-2005042115 A1 * | 5/2005 | ............. A63B 23/14 |
| WO | 2006/033036 | 3/2006 | |
| WO | 2008/032270 | 3/2008 | |

OTHER PUBLICATIONS

Written Opinion of the ISA for PCT/EP2021/071926, mailed Nov. 25, 2021, 7 pages.

* cited by examiner

4A

4B

4C

REHABILITATION DEVICE AND APPARATUS

This application is the U.S. national phase of International Application No. PCT/EP2021/071926 filed Aug. 5, 2021, which designated the U.S. and claims priority to EP Patent Application No. 20190084.2 filed Aug. 7, 2020, the entire contents of each of which are hereby incorporated by reference.

FIELD OF INVENTION

The present invention pertains to the field of motor and cognitive rehabilitation of a subject. In particular, the invention relates to a device for upper limbs rehabilitation and/or upper limbs assessment and a method for assessing the upper limbs of a subject.

BACKGROUND OF INVENTION

Stroke is currently the major cause of long-term disability. One in six people worldwide will experience a stroke during their lifetime and every year, 15 million people worldwide have a stroke. Moreover, the absolute number of strokes is continuously increasing because of the ageing population.

The annual healthcare costs related to stroke incidents is estimated at around EUR 30 billion in Europe and EUR 57 billion in the United States of America; 5% of which is related to post-stroke rehabilitation, i.e. EUR 1.5 billion and EUR 2.85 billion in Europe and USA, respectively.

The physical effects of stroke are variable and may include impairment of motor function that usually involves paralysis or paresis of the muscles on the side of the body that is contralateral to the side of the brain lesion. Impairment of the upper limbs is of special concern because of the impact of upper extremity impairments on disability, independence, and quality of life. Besides stroke, other incidents may cause a significant impairment of the upper limbs, thereby resulting in severe disability. These incidents include, but are not limited to: traumatic brain injury, spinal cord injury, brain tumor, Parkinson's disease, chronic diseases, such as for example multiple sclerosis, cerebral palsy, motor neuron diseases, such as for example amyotrophic lateral sclerosis, meningitis, encephalitis, muscular dystrophies, paralysis caused by a herniated cervical disc, fractures and lesions of the bones of the upper limb during the remodeling phase.

In order to recover or retain functional ability after a stroke or another incident affecting the upper limbs, patients usually undergo physical rehabilitation therapy with a therapist. However, physical rehabilitation relies on the therapist's personal experience, it does not provide high intensity and high repetition training, and it does not provide a quantitative and objective evaluation of the subject condition and of his/her progress.

Several devices providing an interactive upper limb rehabilitation have been developed, with the aim to provide standardized rehabilitation exercises, to collect data, to provide intensive and/or repetitive exercises.

These devices may comprise an interactive screen, and provide therapeutic games which involve the interaction of a user with said screen. This is typically achieved via stereotyped exercise, which are limited with respect to many aspects, from the type of exercise, to the type of user interaction (e.g., pressing, tapping, dragging), as well as the recognizable touch inputs (e.g., fingers, or stylus).

Therefore, these devices are inadequate to provide the minimum level of user-customization which is required in a medical context, such as in post-stroke rehabilitation. Moreover, they are not adapted to provide objective measurements of the functionality of the upper limbs of the user who is interacting with the screen.

Of note, an objective and accurate assessment of the upper limbs is desirable not only in a medical context but also in several applications such as neurosciences, pediatric (or child development) monitoring and research, sport, education.

The present invention relates to a device that solves the problems of the prior art. In particular, the present invention provides a device for upper limb rehabilitation and/or assessment and a method for assessing the upper limbs of a subject.

Moreover, it relates to a device that involve the use of a large number of objects, also comprising everyday objects.

SUMMARY

The present invention relates to a device for assessing and/or rehabilitating the upper limbs of a subject, said device comprising a display surface, a detection surface, and a processing unit, wherein:
  the display surface is configured to display at least one predefined shape having a predefined position and a predefined orientation with respect to the display surface;
  the detection surface comprises an array of light emitters arranged to generate a grid of light beams on the display surface, and an array of light detectors, each light detector being configured to detect the light beam from a respective light emitter and to generate a signal representative of the detected light; and
  the processing unit is configured to:
    receive as input the signal generated from the light detectors;
    based on the received signal, determine the presence of an object obstructing at least one light beam on the detection surface;
    if the presence of an object is determined, determine the position, the orientation and the shape of the object;
    calculate a similarity metrics based on at least one of the predefined position, orientation and shape of the shape displayed on the display surface and respectively at least one of the previously determined position, orientation and shape of the object.

Advantageously, by calculating a similarity metrics between the shape displayed on the display surface and the shape of the object it is possible to quantitatively and objectively assess the subject's upper limbs. In other words, it is possible to assess the subject's upper limbs by evaluating how similar is the object that he/she placed on the surface of the device, with respect to expected position, orientation and shape.

Moreover, the specific arrangement of the light emitters and detectors, which form a grid of light beams on the detection surface, allows to rapidly and simultaneously detect a large number of contact points. More precisely, contact events are detected because they cause light interruption on one or more light beams of the grid.

In particular, the detection surface of the present invention allows to simultaneously detect more than 30 contact points.

This would not be possible with resistive detection surfaces, or with surface acoustic wave detection surfaces, which do not recognize multi-touch gestures. In addition, resistive detection surfaces have low sensitivity, because a pressure on the screen is required.

Moreover, the present device is capable of determining the shape, orientation and position of any object. This is not be possible with capacitive screens, because they can only detect conductive materials. Accordingly, capacitive screens can only be used with specific conductive objects.

Of note, these specific objects are typically designed so as to optimize their interaction with a predetermined screen, and compatibility with other screens is not contemplated.

As a consequence, the choice of the objects relies on the catalogue assortment of the vendor and on the economic means of the buyer, e.g., the end-user or a therapist. Moreover, the limited objects' number and variety are non-negligible constraints that may affect the quality and variety of exercises which may be provided to the end-user (for instance, in a context of rehabilitation therapy), as well as the number of cognitive or motor or cognitive capacities which may be assessed.

The present invention also relates to a system for assessing and/or rehabilitating the upper limbs of a subject, the system comprising the device described hereinabove and at least one object, the object comprising an object support, the device-side of the object support comprising supporting legs being a pattern of obstacles configured to minimize the obstruction of the light beams of the grid, and wherein the processing unit is further configured to:

receive as input a library of patterns wherein each pattern is associated with at least one object property;

based on the signal generated from the light detectors, determine the presence of a pattern of obstacles of an object support on the detection surface;

if the pattern of obstacles matches a pattern in the library, determine a property of the object, said property of the object being the at least one object property associated with the matching pattern in the library.

Advantageously, the object support having legs configured to minimize the light beam obstruction allows to increase the number of objects which may be detected.

In one embodiment, the display surface is configured to display at least one predefined property that does not affect the light beam obstruction, and the processing unit is further configured to:

calculate a similarity metrics based on the determined property of the object, and the predefined property.

In this case, the determined property of the object is the at least one object property associated with the matching pattern in the library.

Advantageously, this embodiment allows to identify a property of an object resting on the object support based on the pattern of obstacles.

Moreover, this embodiment allows to identify a property of an object resting on the object support that does not affect the light beam obstruction. In this embodiment, each pattern of obstacles stored in the library may be associated with a property that does not affect light beam obstruction, such as the color. For example, a first pattern of obstacle may be associated with the color "red" and a second pattern of obstacles may be associated with the color "green". In this example, if the color "green" is displayed on the detection surface, the processing unit is capable of determining whether the pattern of obstacles on the detection surface is equal to the pattern in the library that is associated with "green". In one embodiment, the object property is the object color, the object weight, the object temperature, the object texture, or the object material.

In one embodiment, the processing unit is configured to detect at least 5 patterns of obstacles simultaneously. This embodiment allows to detect at least 5 distinct objects.

The present invention also relates to an apparatus comprising a table and a device according to any one of the embodiments described hereabove, wherein the device is installed on the table top of a table, the table comprising means for rotating the table top about a horizontal axis of an angle comprised between 0° and 90°.

This embodiment allows to rotate the table top, thence the device installed on it. The device may be rotated of a predetermined rotation angle which may be selected for instance on the basis of the type of upper limb skill to be assessed.

The present invention also relates to a computer-implemented method for assessment of the upper limbs of a subject. The method comprises the following steps:
a) displaying on a device as described hereinabove at least one predefined shape having a predefined position and a predefined orientation with respect to the display surface;
b) receiving as input the signal generated from the light detectors;
c) based on the received signal, determining presence of an object obstructing at least one light beam on the detection surface;
d) if the presence of an object is determined, determining the position, the orientation and/or the shape of the object;
e) calculating a similarity metrics based on at least one of the predefined position, orientation and shape of the shape displayed on the display surface and respectively at least one of the previously determined position, orientation and shape of the object.

The device may be an interactive screen or touch screen comprising a display surface and a detection surface equipped with an array of light emitters generating a bidimensional grid of light beams, and an array of respective light detectors.

In one embodiment, the interactive screen may comprise a protective surface.

In one embodiment, the step of displaying at least one predefined shape further comprises displaying a predefined property and the method further comprises:

comparing the determined shape of the object with a list of N patterns stored in a library wherein each pattern is associated with at least one object property, N being preferably equal or greater than 5;

if the determined shape of the object matches a pattern in the library, determining a similarity metrics based on the determined shape of the object and the predefined property.

In this case, the determined shape of the object is the object property associated with the matching pattern in the library.

In one embodiment, the method according to the present invention further comprises:
f.1) receiving as input a difficulty level;
f.2) displaying at least one second shape, the at least one second shape being selected from a database of shapes based on the difficulty level and/or on the similarity metrics.

The at least one second shape has a predefined position and a predefined orientation with respect to the display surface. Each of said shape, position and orientation of the second shape may be equal or different from the shape, position and orientation of the previously displayed predefined shape.

In one embodiment, the method according to the present invention further comprises:

f.3) receiving as input a difficulty level;

f.4) rotating the device by an angle, the angle of rotation being calculated based on the difficulty level.

This device may be rotated before or during execution of the exercise, the latter permitting to adapt the difficulty of the exercise in real time.

In one embodiment, the steps b) to f) are periodically repeated and the repetition frequency is calculated based on the difficulty level (i.e., it is a function of the difficulty level). In this embodiment, the steps that are periodically repeated are:

receiving as input the signal generated from the light detectors;

based on the received signal, determining presence of an object obstructing at least one light beam on the detection surface;

if the presence of an object is determined, determine the position, the orientation and/or the shape of the object;

calculate a similarity metrics based on at least one of the predefined position, orientation and shape of the shape displayed on the display surface and respectively at least one of the previously determined position, orientation and shape of the object;

receiving as input a difficulty level;

displaying at least one second shape, the at least one second shape being selected from a database of shapes based on the difficulty level and/or on the similarity metrics; and/or rotating the interactive screen by an angle, the angle of rotation being calculated based on the difficulty level.

The present invention also relates to a computer-implemented method for assessing the upper limbs of a subject, the method comprising the following steps:

displaying on a device as described here above at least one target trajectory comprising a starting point, an end point and optionally, a line connecting the starting point and the end point;

receiving as input the signal generated from the light detectors;

based on the received signal, determining the presence of an object obstructing at least one light beam on the detection surface;

if the presence of an object being displaced on the device is determined, determine the position of the object, so as to obtain an object trajectory comprising an initial object position and a final object position;

calculating a first distance between the initial object position and the starting point of the target trajectory, and a second distance between the final object position and the end point of the target trajectory;

optionally, displaying on the display surface a feedback based on the first distance and/or the second distance.

This embodiment allows to assess the upper limbs of a subject who is performing a bimanual exercise consisting in moving an object on the device while reproducing a target trajectory therein displayed.

In one embodiment, the method according to the present invention, further comprises the following steps:

at regular time intervals, based on the received signal, determining the position of the object displaced on the device, so as to obtain an object trajectory comprising the initial object position, a plurality of intermediate object positions and the final object position;

for each intermediate object position, calculating the distance between said position and the target trajectory;

optionally, displaying on the device a feedback based on the calculated distance.

This embodiment allows to assess the ability to follow the entire displayed trajectory with the object.

The present invention also relates to a computer program product for assessment of the upper limbs of a subject, the computer program product comprising instructions which, when the program is executed by a computer, cause the computer to carry out the steps of the method described hereabove.

The present invention also relates to a computer-readable storage medium comprising instructions which, when the program is executed by a computer, cause the computer to carry out the steps of the method described hereabove.

Definitions

In the present invention, the following terms have the following meanings:

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, more preferably of 5 percent.

The term "subject" refers to a mammal, preferably a human. In one embodiment, the subject may be a "patient", i.e. a subject awaiting the receipt of, or receiving medical care.

The term "rehabilitation exercise" refers to any exercise to be performed by a subject interacting with the device according to the present invention, the exercise comprising placing and/or moving an object on the device surface so as to reproduce a task.

The term "rehabilitation session" refers to a series of rehabilitation exercises.

DESCRIPTION OF THE DRAWINGS

The present disclosure will be better understood, and other specific features and advantages will emerge upon reading the following description of particular and non-restrictive illustrative embodiments, the description making reference to the annexed drawings wherein.

DETAILED DESCRIPTION

The following detailed description will be better understood when read in conjunction with the drawings. For the purpose of illustrating, the device is shown in the preferred embodiments. It should be understood, however that the application is not limited to the precise arrangements, structures, features, embodiments, and aspect shown. The drawings are not drawn to scale and are not intended to limit the scope of the claims to the embodiments depicted. Accordingly, it should be understood that where features mentioned in the appended claims are followed by reference signs, such signs are included solely for the purpose of enhancing the intelligibility of the claims and are in no way limiting on the scope of the claims.

Figure 1:
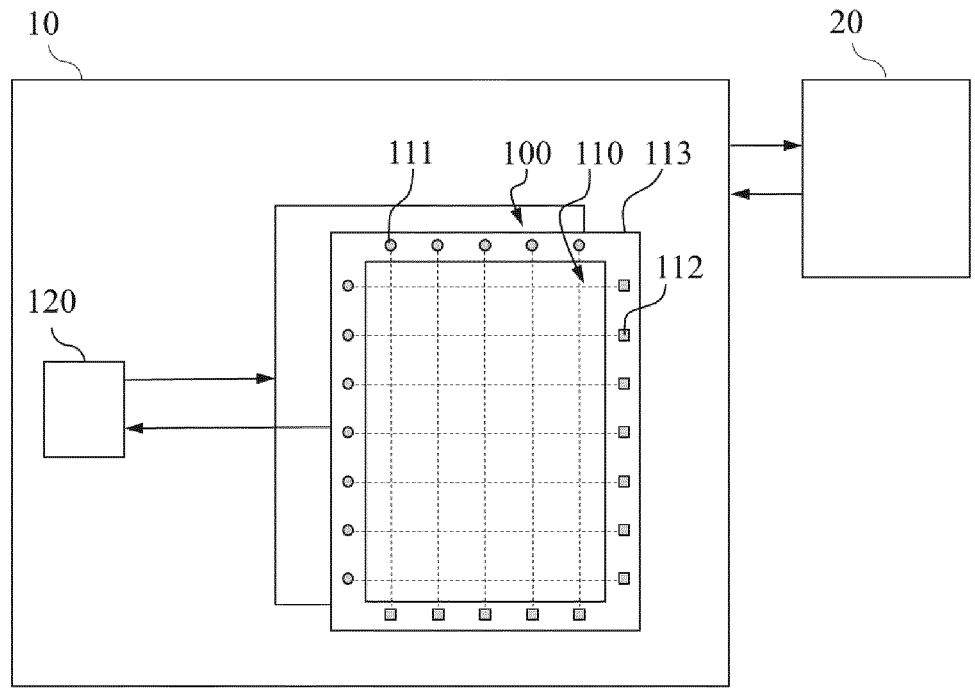
FIG. 1 is a block diagram schematically showing a device 10 according to the present invention interacting with a remote device 20.

As can be seen in FIG. 1, a device 10 according to the present invention comprises: a display surface 100, a detection surface 110, and a processing unit 120.

Figure 4:
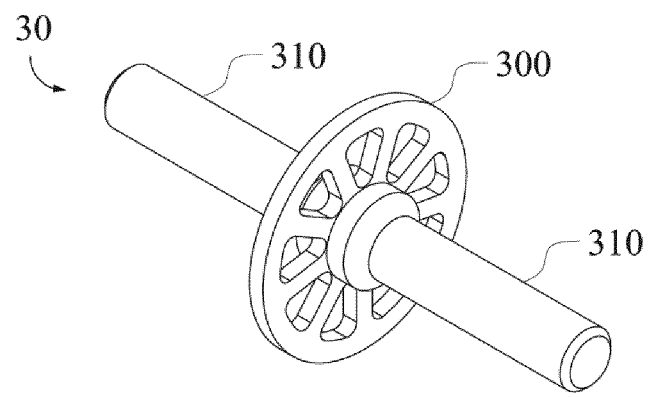
FIG. 4A FIG. 4B and FIG. 4C are a perspective views of an object 30 according to three exemplary embodiments.
Figure 4:
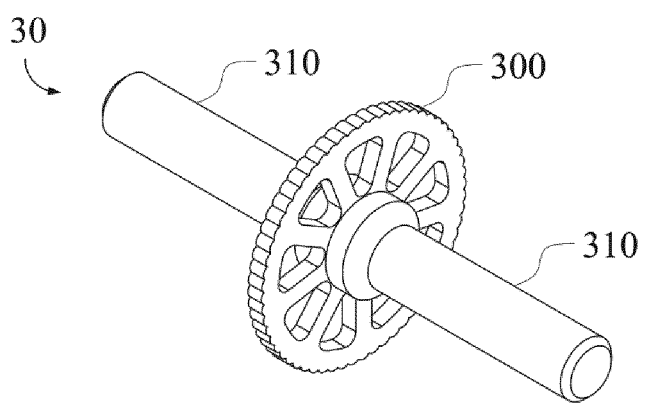
Figure 4:
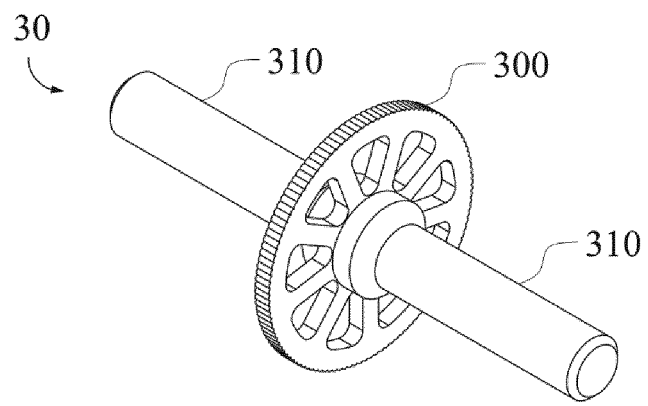

In order to perform an exercise, the subject has to interact with the detection surface 110 of the device 10 while reproducing the task that is displayed on the display surface 100. The display surface 100 is configured to display the task in various forms, such as shapes, trajectories, or physical properties. The subject interaction with the detection surface 110 to reproduce the task, may involve the use of one or more objects 30 (FIG. 4). The processing unit 120 is capable of determining whether the interaction of the subject with the detection surface 110 correspond to the displayed task.

The device 10 may be connected via a wired or wireless network to a peripheral device 20, such as a for example a professional computer. The peripheral device may be a therapist-side device 20 so that a therapist may remotely control the processing unit 120 of the device 10. For instance, the therapist may remotely trigger the display of a rehabilitation exercise on the display surface 100 of the present device 10. This embodiment is particularly advantageous to perform a telerehabilitation session.

Figure 2:
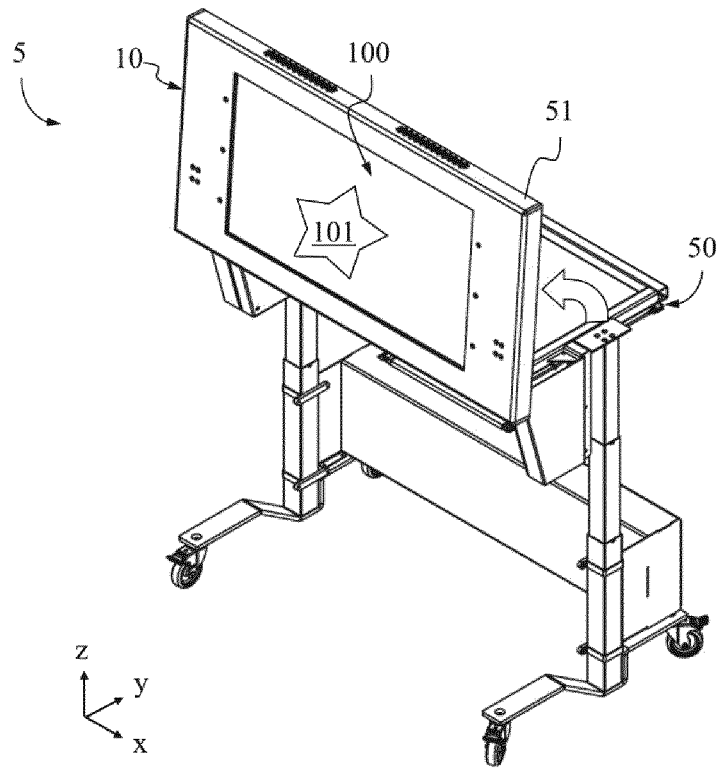
FIG. 2 is a perspective view of an apparatus 5 comprising a device 10 according to the present invention mounted on a table 50.
Figure 3:
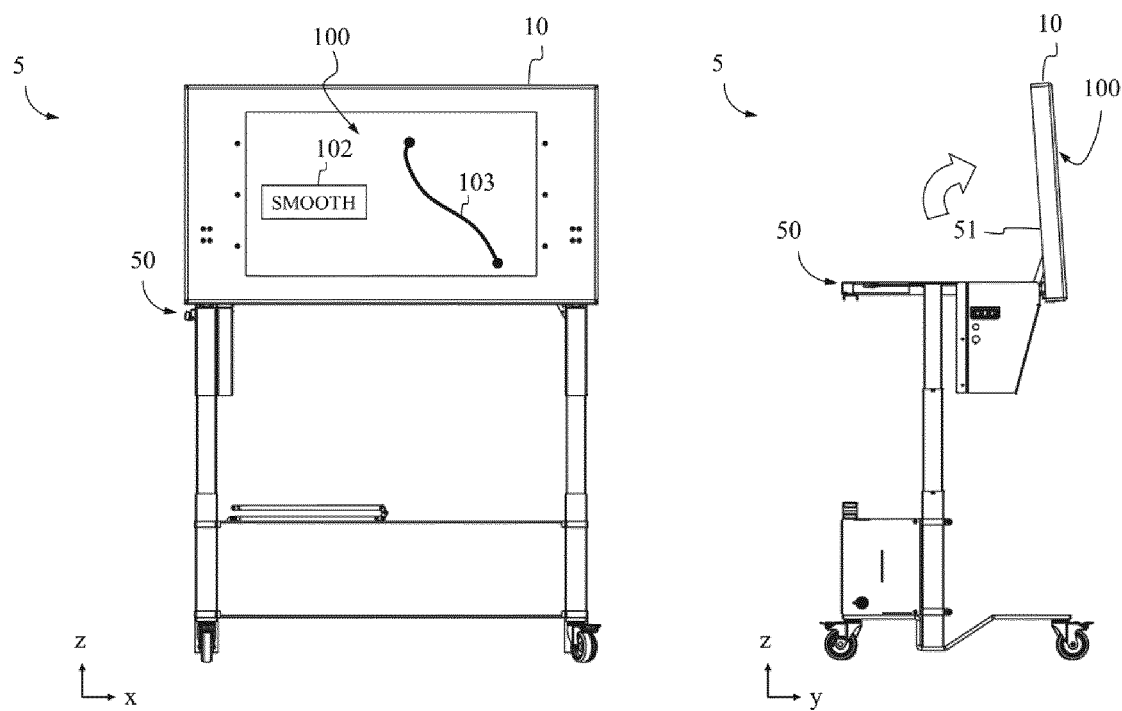
FIG. 3A is a frontal view of the apparatus 5 of FIG. 3.
FIG. 3B is a lateral view of said apparatus 5.

In one embodiment, the display surface 100 is configured to display at least one predetermined shape 101 (FIG. 2). In one embodiment, the display surface 100 may be configured to display a predefined property 102 or a target trajectory 103 (FIG. 3).

The display surface 100 can be, for example, a screen, a monitor or a television. According to one embodiment, the display surface 100 of the present device 10 displays a graphical user interface (GUI) with a user-friendly environment.

According to one embodiment, the display surface 100 of the present device 10 is capable of displaying a first and a second GUI, so as to provide a subject-side and a therapist-side GUI, respectively.

The subject-side GUI allows to display the at least one property 102 as described hereabove in a videogame environment. The display of the videogame may be triggered by the processing unit 120.

The therapist-side GUI may allow the therapist to perform one or more of the following operations: control the processing unit 120; visualize the movements performed by the subject; select, or design himself/herself, the predefined shape and/or the target trajectory to be displayed on the display surface 100.

According to one embodiment, the display surface 100 and the detection surface 110 form a rectangular interactive screen. In one embodiment, the diagonal of the interactive surface is inferior or equal to 90 inches, preferably 55 inches, 50 inches, 45 inches, or 40 inches. In one embodiment, the diagonal of the interactive surface is inferior to 228.6 centimeters (cm), 139.7 cm, 127 cm, 114.3 cm or 101.6 cm. In a preferred embodiment, the diagonal of the interactive surface is equal to 40 inches, i.e. 101.6 cm. The large surface enables full flexion and extension movements of the upper limbs.

In one embodiment, the diagonal of the interactive surface is inferior or equal to 32 inches, i.e. 81.3 cm. In this embodiment, the diagonal of the interactive surface is preferably comprised between 21.5 inches and 32 inches, i.e. between 54.6 cm and 81.3 cm. Advantageously, this embodiment allows to provide a portable rehabilitation device.

As shown in FIG. 1, the detection surface 110 comprises an array of light emitters 111 arranged to generate a grid of light beams on the display surface 100, and an array of light detectors 112, each light detector being configured to detect the light beam from a respective light emitter 111 and to generate a signal representative of the detected light.

More precisely, in the device 10 of FIG. 1 the detection surface 110 is the area delimited by a frame 113 and occupied by a grid of light beams as described hereinabove. In this particular example, the frame 113 is on top of the display surface 100 and the arrays of light emitters 111 and detectors 112 are embedded in the frame 113.

As aforementioned, the interaction of the subject with the detection surface 110 may involve the use of objects 30 (FIG. 4).

The presence of an object 30 on the detection surface 110 causes obstruction of one or more light beams of the grid. The light beam obstruction results in a decrease in the light detected by the light detectors 112, hence in the signal that they generate. This signal is transmitted to the processing unit 120 of the device 10 which, based on the received signal, determines the presence of an object 30 in contact with the detection surface 110.

In a preferred embodiment, the light emitters are infrared LEDs. In one embodiment, the light emitters emit an infrared radiation from about 700 nm to about 1000 nm, preferably from about 780 nm to about 980 nm. In one preferred embodiment, the light emitters are configured to emit an infrared radiation of about 850 nm or 940 nm. In one embodiment, these infrared radiation wavelengths refer to the centroid wavelengths or to the peak wavelengths of the light emitters at their operating temperature.

In the embodiment of infrared LEDs, the detection surface 110 is an infrared grid-based detection surface 110 capable of simultaneously detecting a plurality of contact points. In particular, the detection surface 110 of the present invention advantageously allows to simultaneously detect more than 30 contact points. In one embodiment, it is capable of detecting at least 50 contact points.

Moreover, contrarily to capacitive detection surfaces, which are sensitive to conductive objects, infrared-based detection surfaces allow to use objects 30 of any material to generate light beam obstruction. Therefore, the subject can freely select among a plurality of different objects, which objects 30 she/he will use to interact with the detection surface 110 of the present device. Such variety, and the possibility for the subject to choose one or more objects 30 from the variety, improve the functional outcome of the therapy.

Advantageously, in the present invention the variety of objects 30 allows to perform different tasks and, accordingly, to evaluate several upper limb skills, such as manual dexterity, kinematics (e.g., fluidity, linearity, speed and precision of movements), or range of motions.

Moreover, such variety allows to improve the functional outcome of rehabilitation therapy.

Rehabilitation therapies relying on "stand-alone" exercises are not centered on the everyday life difficulties of the subject, but they are rather center on the subject's motor difficulties. As a result, they may help to improve motor outcomes, such as for example strength and dexterity, but the functional outcome is limited.

The device 10 according to the present invention is configured to provide rehabilitation exercises that maximize the functional outcome. This is achieved via the use of objects 30. Moreover, the present device is capable of displaying therapeutic videogames that are chosen according to the specificity of the objects 30, i.e. according to characteristics such as size and shape.

As a result, the device 10 allows the subject to manipulate such objects 30 in an environment that allows him/her to evolve while playing. This is not possible with rehabilitation devices providing "stand alone" exercises. Moreover, the videogames are based (i.e., customized) on the characteristics of the objects 30.

In one embodiment, the objects 30 are selected among everyday objects.

Advantageously, the objects 30 may be selected among personal objects, that is, objects belonging to the subject. This is especially useful when the subject is a child using his/her own toys to interact with the device 10. The use of personal toys may in fact have a positive psychological effect and, in a rehabilitation context, it may improve the effectiveness of the rehabilitation therapy.

The processing unit 120 is configured perform several operations that will be described in more details here below.

Preferably, the processing unit 120 is configured to:
receive as input the signal generated from the light detectors 112;
based on the received signal, determine the presence of an object 30 obstructing at least one light beam on the detection surface 110;
if the presence of an object 30 is determined, determine its position, orientation and shape;
calculate a similarity metrics based on at least one of the predefined position, orientation and shape of the shape 101 displayed on the display surface 100 and respectively at least one of the previously determined position, orientation and shape of the object 30.

In other words, the processing unit 120 is configured to compare the determined position, orientation and shape of the displayed shape with those of the object 30; and based on the comparison, to calculate a similarity metrics.

The term "similar" refers to two objects A and B sharing at least one property which is measurable and which may take comparable values in A and in B. Accordingly, "similarity metrics" herein refers to a real-valued function that quantifies the similarity between two objects A and B, and which is calculated as a function of at least one property P that is shared by the two objects.

Therefore, a similarity metrics may be defined as $S=f(P_A; P_B)$, wherein $P_A$ is property of the object A, and $P_B$ is the corresponding property of the object B.

It should be understood that the term "property" herein is not limited to measurable properties (i.e., properties which may be compared against a standard unit of measurement), but it relates in a general way to any property which may take comparable values in distinct objects and/or which may be compared against a standardized set of properties universally accepted as reference (e.g., the primary colors).

Accordingly, said property may include, without limitation: length, mass, temperature, volume, hardness, shape, color, texture, odor, orientation, position and the like.

More precisely, in the present disclosure the similarity metrics quantifies the similarity between a predetermined property (or more properties) of the displayed shape, and the respective property (or properties) of the object on the detection surface 110.

Unless otherwise specified, in the present disclosure by "predefined property" 102 (which is also called displayed property) it is meant a property displayed on the display surface 100; whereas by "object property" it is meant a property that is associated with a reference pattern stored in a library (the patterns and their corresponding properties may be for instance the records of a relational database).

The present invention allows to determine a real property of a specific object 30 (for instance its shape) and determine whether said property is similar to the aforementioned displayed properties 102 and/or the object properties stored in the library, as will be later described.

Indeed, in the present invention, the interaction of the subject with the detection surface 110 may comprise placing an object 30, and optionally moving said object 30, on the detection surface 110, so as to perform a rehabilitation exercise. In one embodiment, the object 30 is placed directly on the detection surface 110.

The present invention also relates to a system for assessing and/or rehabilitating the upper limbs of a subject, the system comprising the device 10 and at least one object 30, preferably a set of objects 30.

The present invention also relates to an apparatus 5 for upper limb assessment and/or rehabilitation.

FIG. 2 illustrates an apparatus 5 for assessment of the upper limbs.

The apparatus comprises a table 50 and a device 10 is installed on the table top 51.

To ensure a simple use of the apparatus 5 by the subject, the device 10 is mounted in a pivotable and/or height-variable table 50.

In order to pivot the device 10, in particular about an axis running parallel to the floor in a longitudinal direction of the device 10, a pivot device known from the prior art is provided for this purpose.

Advantageously, the table 50 may comprise means for rotating the table top 51 about a horizontal axis x of an angle comprised between 0° and 90°, wherein 0° corresponds to a horizontal table top and 90° corresponds to a vertical table top 51. This embodiment allows to automatically rotate the table top 51 of a predetermined rotation angle. Said rotational motion may be imposed while the subject is performing a bimanual task. Different rotation angles are associated with different degrees of task difficulty and/or with different upper limb movements.

In one embodiment, the means for rotating the table top 51 are motorized means. In another embodiment, the means for rotating the table top 51 are activated manually.

In one embodiment, the rotation angle is selected by the therapist.

In order to vertically translate the device 10, a lifting device known from the prior art is provided for lifting and lowering the device 10.

In one embodiment, the table 50 further comprises means for translating the table top 51 along a vertical axis z, so as to adjust the height of the table top 51, such as for example telescopic table legs. Preferentially, the means for translating the table top 51 allow to adjust the height of the table top 51 between 400 mm and 1250 mm, preferably between 550 mm et 1100 mm. This ensures that the subject may perform rehabilitation exercises while installed in a specific position.

Therefore, the space for the subject's legs is not reduced during the rotation of the table top 51.

In one embodiment, the translation means and/or the rotation means of the rehabilitation apparatus 5 comprise a security mechanism configured to detect a risk for the subject arising from the translation and/or the rotation of the table top 51. The security mechanism allows to prevent starting or to stop the rotating means and/or the translating means if such risk is detected.

As wan be seen in FIG. 2, in one particular embodiment, the table 50 further comprises at least two pairs of casters. Preferentially, the casters are swivel casters comprising caster wheel brakes to easily move and install the table 50. This allows to provide a transportable device 10, that can be handled and transported by one person. This embodiment is particularly advantageous for providing a bimanual rehabilitation apparatus 5 for rehabilitation and/or assessment of the upper limbs which may be transported by a therapist.

In one embodiment, the table 50 further comprises loudspeakers, for example to acoustically transmit operating instructions to the subject.

FIG. 3A is a frontal view of an apparatus 5 according to the present disclosure. In this example, a predefined property 102 and a target trajectory 103 are displayed on the display surface 100. Accordingly, the user interacting with the apparatus 5 may use an object 30 compliant with the displayed property 102 (such as the object of FIG. 4A) to reproduce the target trajectory 103.

In this example, the displayed property 102 is as textual element. However, in some embodiments, the displayed property 102 may be a different audio or visual element.

FIG. 3B is a lateral view of the apparatus 5 of FIG. 3A wherein the rotation of the table top 51 is better shown.

FIG. 4A FIG. 4B and FIG. 4C are a perspective views of three exemplary objects 30. More precisely, the objects 30 therein illustrated comprise a wheel 300 having at both ends of its axis of symmetry two handles 310. Thus, the wheel 300 allows to place the object 30 in contact with the device 10, and the handles 310 to move said object 30 on the device 10, for instance to reproduce a displayed trajectory 103.

The wheel 300 of the object 30 of FIG. 4A is smooth, whereas the wheels 310 of the objects 30 of FIGS. 4B and 4C have different textures.

As can be seen in FIGS. 4B and 4C, the textured wheels 300 may have teeth arranged at regular distances on their outer circumference. In these examples, the distance between adjacent teeth is greater in the wheel of FIG. 4B compared to the wheel 300 of FIG. 4C.

In his case, the device 10 may be capable of recognizing different wheels 300 according to the size and spacing of the teeth present on the circumference.

This embodiment is particularly advantageous to differentiate two users who simultaneously interact with the device 10 through two distinct wheels 300 characterized by different spacing and tooth size.

In one embodiment, the object 30 stands on an object support 40.

FIG. 5A and FIG. 5B are respectively a bottom view and a lateral view of a support 40 according to a first embodiment in which the support 40 comprises a flat surface 10 (in this case, a circle) and supporting legs 410.

Said supporting legs 410 are arranged to create a first pattern of obstacles that minimizes the light beam obstruction.

FIG. 6A and FIG. 6B are respectively a bottom view and a lateral view of an object support 40 according to a second embodiment in which the flat surface 400 is a circle and the supporting legs 410 are arranged to create a second pattern of obstacles that minimizes the light beam obstruction.

The object support 40 comprises a flat surface 400, on which the object 30 stands, resting on three or more supporting legs 410. The supporting legs 410 are spaced from each other at predetermined distances, so that when the object support 40 is placed on the detection surface 110, they create a pattern of obstacles configured to minimize the light beam obstruction.

Figure 5:
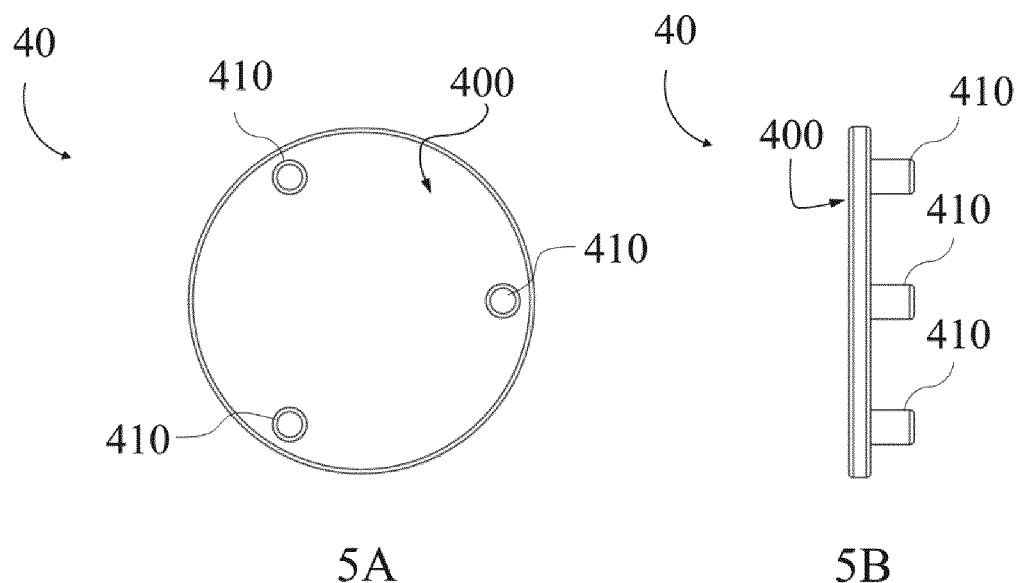
FIG. 5A and FIG. 5B are respectively a bottom view and a lateral view of an object support 40 according to a first embodiment.

A first example of said pattern of obstacles that minimizes light beam obstruction is provided by the legs 410 of FIG. 5. A second example of a pattern of obstacles that minimizes light beam obstruction is provided by the legs illustrated in FIG. 6.

Figure 6:
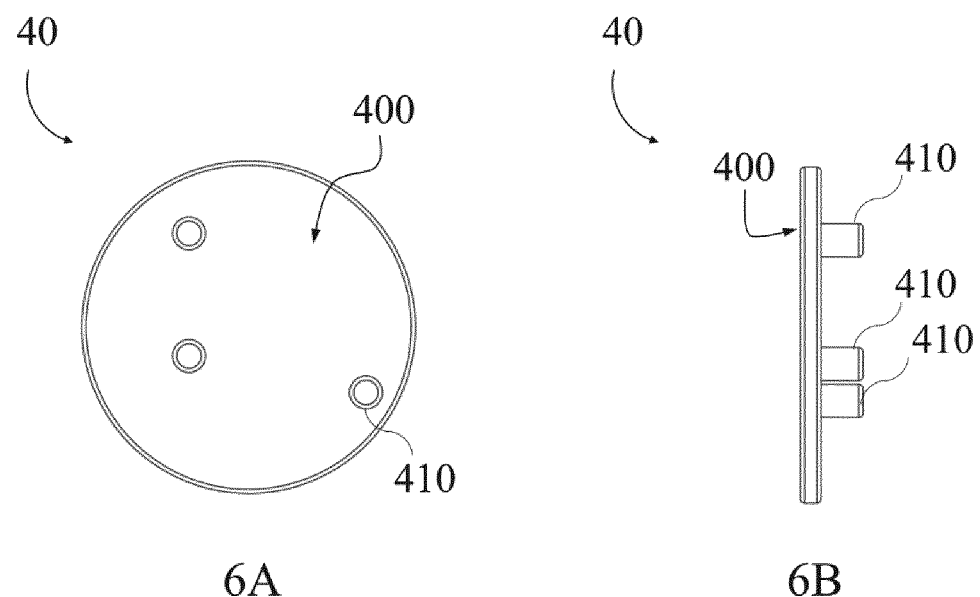
FIG. 6A and FIG. 6B are respectively a bottom view and a lateral view of an object support 40 according to a second embodiment.
Figure 7:
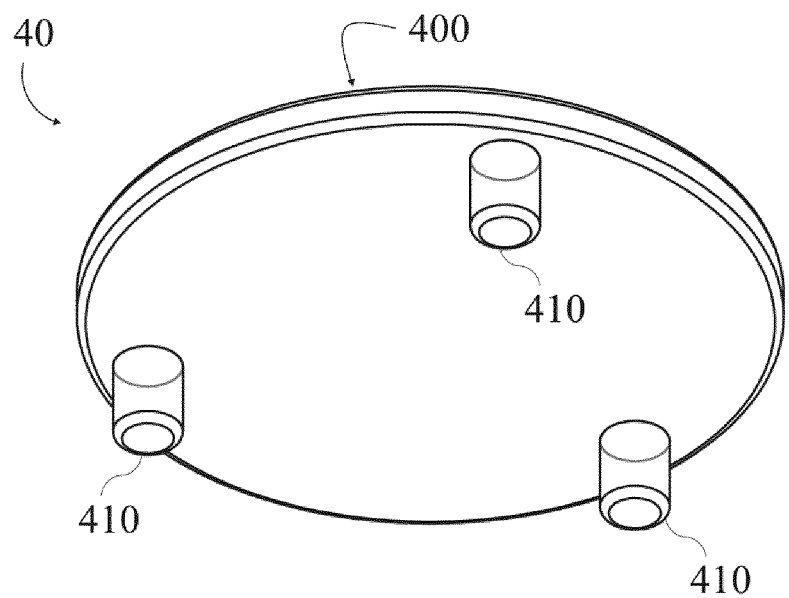
FIG. 7 is a perspective view of the object support 40 illustrated in FIG. 4.
Figure 8:
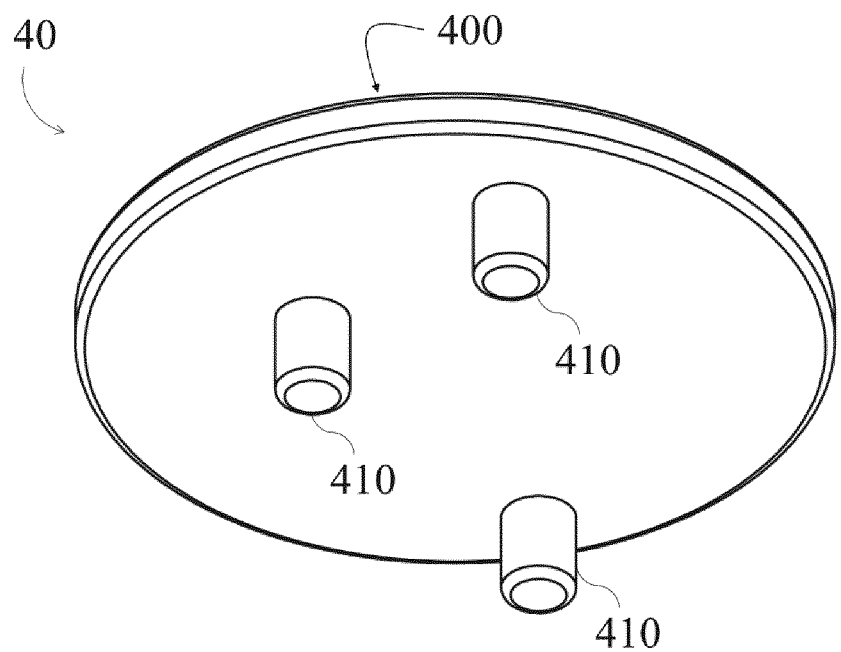
FIG. 8 is a perspective view of the object support 40 illustrated in FIG. 5.

FIG. 7 and FIG. 8, which are perspective views of the object supports 40 represented in FIG. 5 and FIG. 6, respectively.

The flat surface 400 of the object support 40 may be a circle.

However, in some embodiments, the surface 400 may have different shapes, for instance it may be polygonal.

In one embodiment, the processing unit 120 is capable of recognizing whether the light obstruction is caused by an object 30 or a by an object support 40. For instance, after determining the shape of an object 30 obstructing at least one light beam In one embodiment, the object support 40 is detachable from the display surface 100. This has the advantage of offering the possibility to use the object support 40 or not.

In a preferred embodiment, the object support 40 comprises three supporting legs 410, thereby ensuring the object 30 stability while minimizing the light beam obstruction. Examples of this embodiment are illustrated in FIGS. 5 to 8.

The supporting legs 410 may be of any shape.

For instance, as can be seen in FIGS. 5 to 8, the supporting legs 410 may be cylindrical. In one embodiment, the cylindrical legs have a diameter inferior or equal to 0.8 cm. In one embodiment, the cylindrical legs have a diameter superior or equal to 0.8 cm.

In one embodiment, the supporting legs 410 are square or rectangular. In one embodiment, the square or rectangular legs 410 have a width and a length inferior or equal to 1.1 cm. In one embodiment, the square or rectangular legs 410 have a width and a length superior or equal to 1.1 cm.

In one embodiment, the supporting legs 410 of an object support 40 are identical in size. In another embodiment, the supporting legs 410 of an object support 40 are not identical in size.

The supporting legs 410 of the object support 40 should be high enough, so that when the object support 40 is placed on the detection surface 110, neither the flat surface 400 of the object support 40 nor the object 30 standing on said flat surface 400 cause light beam obstruction. This ensures the creation of a pattern of obstacles that minimizes the light beam obstruction.

In one embodiment, the supporting legs 410 of an object support 40 have a height superior or equal to 1 cm.

In one embodiment, the processing unit 120 is further configured to:
receive as input a library of patterns wherein each pattern is associated with at least one object property;
based on the signal generated from the light detectors 112, determine the presence of a pattern of obstacles in contact with the detection surface 110;
compare the pattern of obstacles with the patterns in the library;
if the pattern of obstacles matches a pattern in the library, determine a property of the object 30, the property of the object 30 being the at least one object property associated with the matching pattern in the library.

Since the pattern of obstacles are configured to minimize light beam obstruction, this embodiment allows to increase the number of detectable objects 30. Moreover, it avoids a loss of information regarding the position, the orientation and the shape of the objects 30.

In one embodiment, the present device 10 may be used with one or more object supports 40. For instance, the device 10 may be used with up to five object supports 40. In one embodiment, the present device may be used with at least five object supports 40. In one embodiment, the present device allows to detect and to accurately identify five or more different objects 30 simultaneously.

Advantageously, the object supports 40 also allow to detect the position, orientation and shape of objects 30 with significantly different sizes. In fact, if objects 30 with significantly different sizes, small and large, are placed on the detection surface 110 in the same light beams, the larger objects 30 would obstruct the smaller ones (e.g., large objects may block one or more light beams before they reach the small objects), resulting in the loss of precision in the determination of the position and shape of the smaller objects 30.

In a preferred embodiment, the object support 40 is reversibly attached to the object 30 via a hook-and-loop attachment mechanism. For instance, the object 30 may comprise a loop surface, and the object-side of the detachable object support 40 may comprise a hook surface.

In one embodiment, the object support 40 may be reversibly attached to the object 30 via magnetic attachment means, or via snap-fitting.

In one embodiment, each of the pattern in the library comprises at least 3 values and the processing unit 120 is configure to compare the pattern of obstacles with the patterns in the library via the following operations:
calculating at least 3 geometric values representative of the pattern of obstacles;
comparing the geometric values with the at least 3 values in the library.

In one embodiment, the geometric values representative of the pattern of obstacles are the distances between the supporting legs 410. In one embodiment, the geometric values representative of the pattern of obstacles are the angles between the segment of lines connecting the supporting legs 410. In one embodiment, the geometric values are a combination of distances and angles as described hereabove.

In one embodiment, each pattern in the library of patterns is associated with at least one preferred orientation. In this embodiment, the processing unit 120 is further configured to:
determine the orientation of the pattern of obstacles in contact with the detection surface 110;
if the pattern of obstacles matches a pattern in the library, compare the determined orientation with the orientation associated with the matching pattern in the library.

The detection surface 110 allows to identify an object 30 based on a property of the object 30 that affects the light beam obstruction, such as the object position and shape. Therefore, it is not possible to identify an object 30 based on properties of the object 30 that do not affect the light beam obstruction, such as for example the color, the temperature, the texture.

However, the object support 40 allows to identify an object 30 on the detection surface 110 based on the pattern of obstacles defined by the legs 410 of the object support 40. In other words, the object support 40 allows to identify an object 30 based on a property associated with the specific pattern of obstacles of said object support 40. This is ensured by the use of a library comprising a list of patterns, wherein each pattern is associated with at least one object property.

The pattern of obstacles that obstructs the light beams (i.e., the legs 410 of the object support 40) is compared to the patterns stored in the library (also called reference patterns), in order to determine a property of the object 30 standing on the object support 40 and/or identify said object 30.

Therefore, the use of an object support 40 allows to identify an object 30 on the detection surface 110 based on a property of the object 30 without limitation to physical properties affecting the light beam obstruction. This allows to increase the variety and/or the complexity of the rehabilitation exercises provided to the subject.

In one embodiment, the display surface 100 is configured to display at least one predefined property 102 that does not affect the light beam obstruction, and the processing unit 120 is configured to:
determine the presence of an object 30 in contact with the detection surface 110 (e.g., detecting a light beam obstruction on the detection surface 110);
based on the signal generated from the light detectors 112, determine the presence of a pattern of obstacles of an object support 40 in contact with the detection surface 110;
compare the pattern of obstacles with the patterns in the library;
determine a property of the object 30, said property of the object 30 being the object property associated with the pattern in the library that matches the pattern of obstacles of the object support 40;

compare the determined property of the object 30 with the predefined property 102 previously displayed;

based on the comparison, calculate a similarity metrics.

In other words, if the pattern of obstacles matches a pattern in the library, the processing unit 120 is configured to determine a property of the object 30, said property of the object 30 being an object property associated with the matching pattern in the library.

The property of the object 30 that does not affect the light beam obstruction may be the object color, the object weight, the object temperature, the object material, or the object texture.

In one embodiment, the display surface 100 may display an object texture such as for example "smooth", "rough", "elastic", "rigid", "adhesive" or a combination thereof.

In one embodiment, the display surface 100 may display an object material such as for example: "rubber", "plastic", "metal", "fabric", "wood", or any combination thereof.

This embodiment allows to provide multi-sensory rehabilitation exercises. In fact, based on the displayed predefined property 102, the device advantageously allows to provide cognitive, visual and/or tactile rehabilitation exercises.

The similarity metrics provides information about the subject's performances, thereby allowing to quantitatively and objectively assess the subject's upper limbs. Moreover, the similarity metrics calculated in successive rehabilitation sessions provides information about the subject's progresses.

According to one embodiment, the similarity metrics is the ratio between the surface of the object that is overlapped with the displayed predefined shape and the total surface of the predefined shape.

The processing unit may calculate the surface of the object based on the number of contact points or based on the determined object shape.

In one embodiment, the surface of the object is the surface of the rectangle that contains all the contact points of the object.

According to one embodiment, the similarity metrics is the distance between the position of the object 30 and the predefined shape or target trajectory 103 displayed on the display surface 100. In a preferred embodiment, the position of the object 30 is the object center. The object center may be the geometric center of the object shape, or it may be the centroid, the circumcenter, the orthocenter or the incenter of the triangle having as vertexes the obstacles of the pattern of obstacles.

In one embodiment, the similarity metrics is a combination of at least two similarity metrics, for instance a combination, such as a linear combination or a polynomial combination, of the surface ratio and the distance defined hereabove.

The similarity metrics allows to provide an upper limb assessment. Depending on the displayed predefined shape 101 or predefined property 102 or target trajectory 103, a specific motor or cognitive skill may be assessed, as better illustrated by the following examples.

Figure 9:
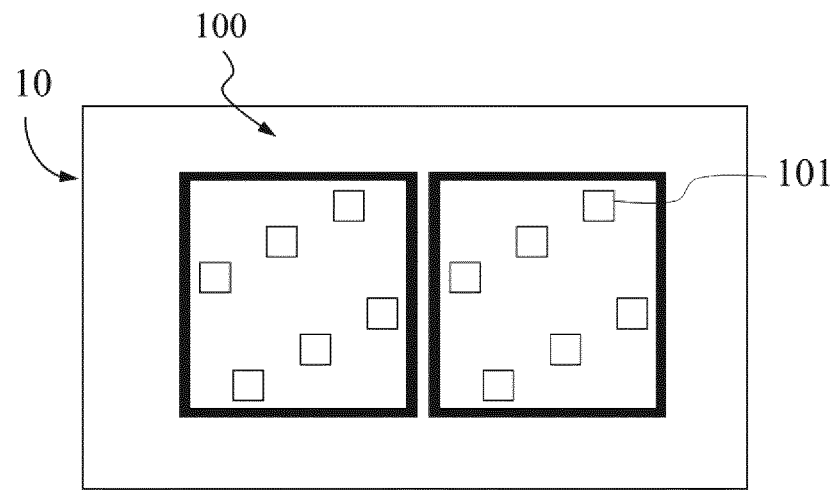
FIG. 9 is a schematic frontal view of the device 10 according to the present invention, while the device is being used for assessing manual dexterity.

FIG. 9 illustrates one example of a device 10 having a display surface 100 on which several shapes 101 are displayed. More precisely, two set of 6 squared shapes spaced apart from each other are displayed. One set of squares is displayed on the left side of the display surface 100, and the other set of squares is displayed on the right side of the display surface 100. This embodiment is particularly advantageous to assess the manual dexterity of the subject, as explained here below.

A first similarity metrics may be calculated based on the overlap between the surface of an object 30 placed by the subject on the display surface 100, and the surface of the displayed square. Accordingly, the similarity metrics will be maximum for an object perfectly overlapped with a displayed square, and minimum for an object 30 which is outside of the displayed squares.

Moreover, it is possible to calculate distinct similarity metrics for the left upper limb that is moving objects 30 on the left side of the display surface 100, and the right upper limb that is moving objects 30 on the right side of the display surface 100. Therefore, it is possible to separately assess the upper limbs.

The similarity metrics may also by calculated by taking into account the time for moving the object 30 from one shape to another. For instance, the similarity metrics may be calculated based on the number of squares reached by an object 30 moved by the subject during a predetermined time. By "reached by the object" it is meant that at least a portion of the object 30 is overlapped with the displayed square 101.

Figure 10:
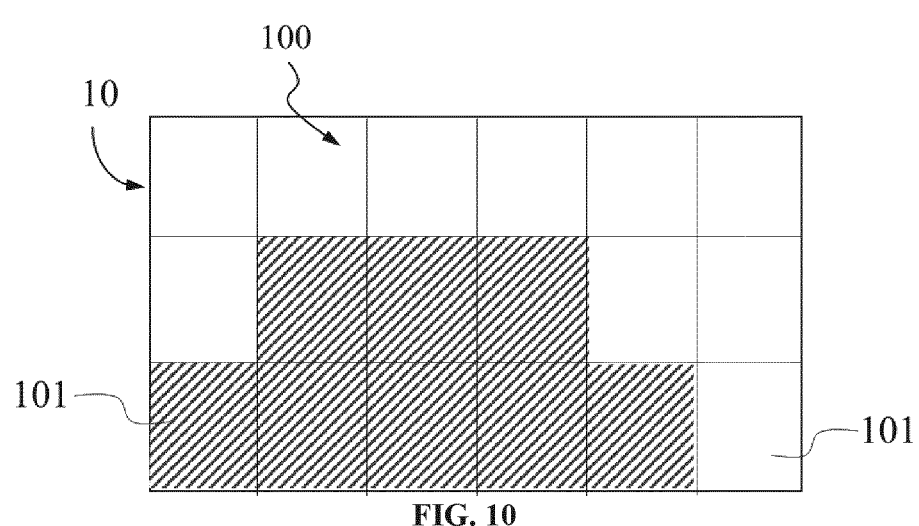
FIG. 10 is a schematic frontal view of the device 10 according to the present invention, while the device is being used for assessing an upper limb range of motion.

FIG. 10 illustrates another example of a device 10 having a display surface 100 on which a matrix made of adjacent shapes 101 (more precisely, of rectangles) is displayed. The rectangles 101 with a hatch pattern represent rectangles 101 of the matrix that are reached by an object 30 moved by the subject. Inversely, the white rectangles 101 represent rectangles 101 that are not reached by the object 30. In this case, the similarity metrics may be calculated for instance on the basis of the ratio between the surface of the hatched rectangles 101, and the total surface of the matrix.

Therefore, this embodiment is particularly advantageous to assess the range of motion.

Figure 11:
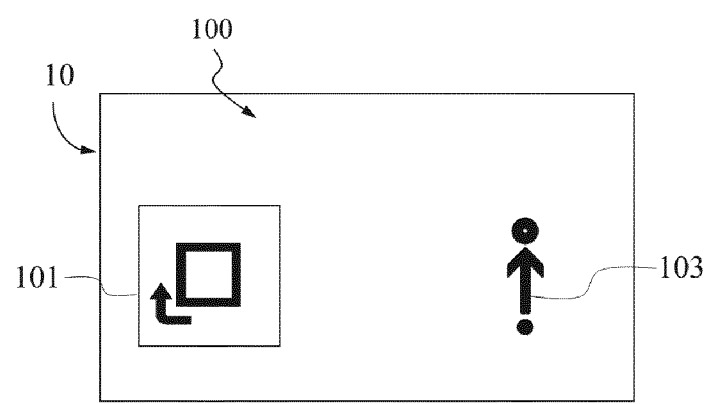
FIG. 11 is a schematic frontal view of the device 10 according to the present invention, while the device is being used for assessing an upper limb kinematics.

FIG. 11 illustrates another example of a device 10 having a display surface 100 on which a squared shape 101 and a liner trajectory 103 are displayed. This embodiment is particularly advantageous to assess various kinematic parameters such as fluidity, linearity, speed and precision of movements.

The shape 101 and trajectory 103 of FIG. 11 may be separately displayed, so as to provide two distinct exercise.

For instance, a first exercise may consist in placing an object on the squared shape, and rotating said object 30 in the direction indicated by the arrow. In this case, the similarity metrics may be calculated based on the object orientation over time, in order to compare it with the expected rotation (arrow).

A second exercise may consist in placing an object 30 of a finger in the initial position (represented by the smaller circle) of the trajectory 103, and moving it towards the final position (represented by the smaller circle) of said trajectory 103. In this case, the similarity metrics may be calculated based on the distance between the initial and final positions of the object 30 and the initial and final positions of the trajectory 103.

In one embodiment, the display surface 100 of the present invention is further configured to display a feedback that indicates whether the exercise was performed correctly. The feedback may be the similarity metrics and/or a function of the similarity metrics.

The feedback may be a function of the similarity metrics and other parameters such as parameters related to the subject and/or parameters related to the task difficulty. In one embodiment, a first visual feedback is displayed if the similarity metrics is below a threshold and a second visual feedback is displayed if the similarity metrics is above said threshold. Said first and second visual feedbacks may be two different colors, such as green and red.

In one embodiment, a feedback indicating that the exercise was performed correctly is displayed if the similarity metrics is comprised within a predefined range of values and feedback indicating that the exercise was not performed correctly is displayed if the similarity metrics is outside the predefined range of values. The range of values may be larger for dynamic exercises and smaller for precision exercises requiring fine upper limb movements.

In one embodiment, the predefined range of values is comprised between 0 cm and 3 cm. This embodiment is particularly advantageous to provide rehabilitations exercises involving fine movements.

In one embodiment, the predefined range of values is comprised between 0 cm and 6 cm. This embodiment is particularly advantageous to provide rehabilitations exercises involving rapid movements.

In one embodiment, the device further comprises a loudspeaker system, and the feedback is an audio-visual feedback.

The feedback may comprise a categorical variable, such as "yes" or "no", a discrete variable, such as an evaluation on a scale of one to ten, or a continuous variable.

In one embodiment, the device further comprises a memory. The memory is configured to store data neutral to the subject, such as a database of shapes, a library of patterns or a list of feedbacks, and data related to a particular subject, such as the calculated similarity metrics, the calculated distances, the displayed feedbacks, the rotation angles. In one embodiment, the memory further stores data relative to the rehabilitation sessions completed by the subjects and/or the future rehabilitation sessions.

In one embodiment, the processing unit is configured to execute an upper limb assessment algorithm to evaluate the upper limbs of the subject based on parameters calculated and/or collected during the rehabilitation session, such as the similarity metrics.

The algorithm may be configured to perform a statistical analysis of the parameters calculated and/or collected during the rehabilitation session.

The present invention also relates to a method for upper limb assessment and/or bimanual rehabilitation of a subject.

Figure 12:
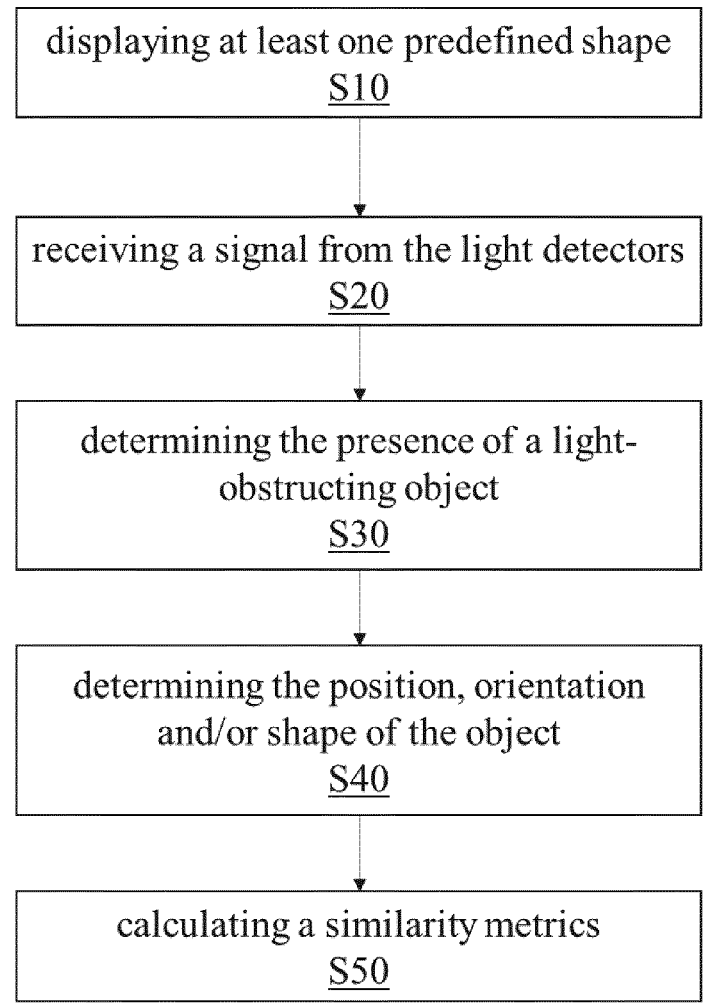
FIG. 12 is a flow chart illustrating an exemplary method for assessment of the upper limbs compliant with the disclosure in which a predefined shape 101 is displayed.

FIG. 12 illustrates the main steps of the method the method compliant with the present disclosure, which comprises:
  a) displaying S10 on a device equipped with an array of light emitters and an array of light detectors as previously described, at least one predefined shape 101 having a predefined position and a predefined orientation with respect to the display surface 100;
  b) receiving S20 as input the signal generated from the light detectors 112;
  c) based on the received signal, determining S30 the presence of an object 30 obstructing at least one light beam on the detection surface 110;
  d) determining S40 the position and/or the shape of the object 30 placed on the interactive screen;
  e) calculating S50 similarity metrics based on at least one of the predefined position, orientation and shape of the shape 101 displayed on the display surface 100 and respectively at least one of the previously determined position, orientation and shape of the object 30.

In other words, the calculation step S50 allows to compare the position and/or the shape of the object 30 with the predefined shape 101 and, based on the comparison, calculate the similarity metrics.

The method allows the subject to perform various type of bimanual rehabilitation exercises. The method also allows to assess the upper limbs. In one embodiment, the at least one predefined shape is provided in a videogame environment, so that the bimanual rehabilitation exercises are performed in the context of games, such as for example city building games.

Figure 13:
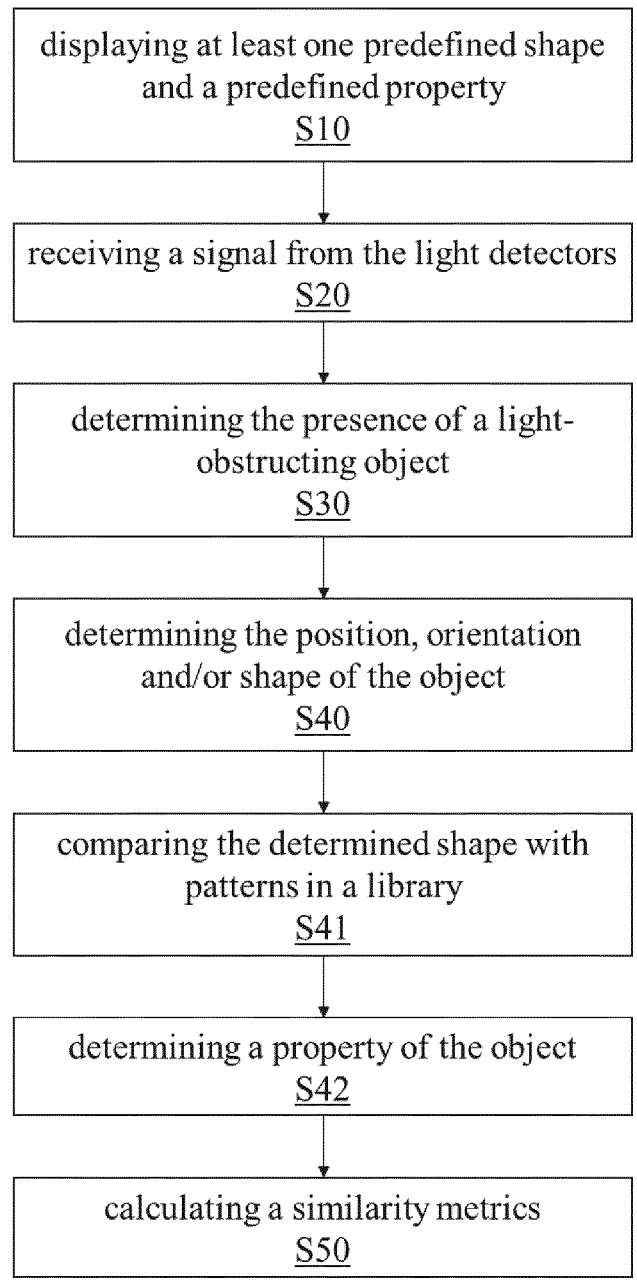
FIG. 13 is a flow chart illustrating an exemplary method for assessment of the upper limbs compliant with the disclosure in which a predefined shape 101 and a predefined property 102 are displayed.

FIG. 13 illustrates one particular embodiment, in which the step of displaying S10 at least one predefined shape 101 further comprises displaying a predefined property 102.

In this case, the method may further comprise:
  comparing S41 the determined shape of the object 30 with a list of patterns stored in a library wherein each pattern is associated with at least one object property;
  if the determined shape of the object 30 matches a pattern in the library, determining S42 a property of the object 30, said property of the object 30 being the object property associated with the matching pattern in the library.

In other words, the determination step S42 allows to determine whether the at least one object property associated with the matching pattern in the library is similar to the displayed object property 102.

The method of FIG. 13 is particularly adapted for upper limb assessment of a subject who is placing, and optionally moving, an object 30 standing on an object support 40 on the device 10.

The library preferentially comprises at least 3, 4 or 5 patterns.

In one embodiment, the method of the present invention further comprises a step of displaying at least one second predefined shape 101, said at least one second predefined shape being selected from a database of shapes based on the similarity metrics.

Figure 14:
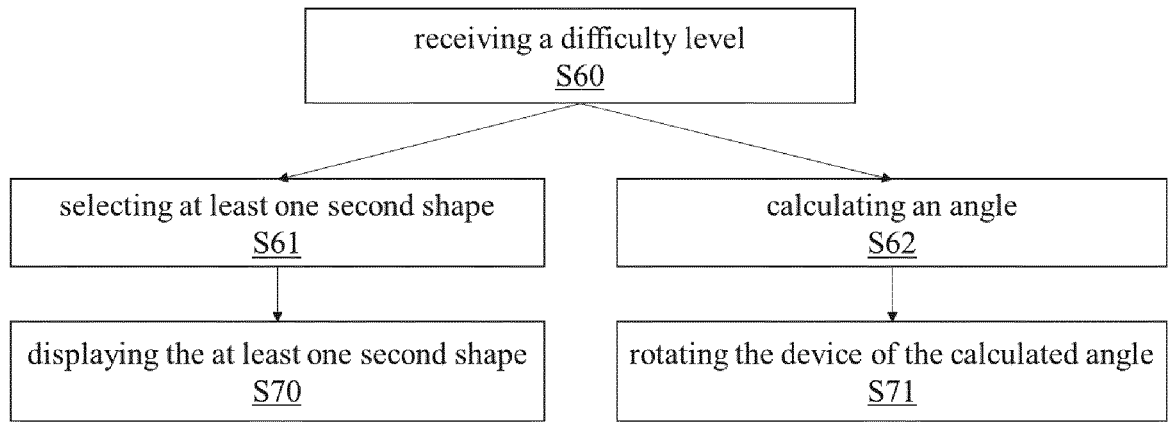
FIG. 14 is a flow chart illustrating an exemplary method for assessment of the upper limbs compliant with the disclosure in which a difficulty level is received.

FIG. 14 illustrates one particular embodiment, in which the method further comprises:
  f.1) receiving S60 as input a difficulty level;
  f.2) displaying S70 at least one second shape 101, the at least one second shape 101 being selected S61 from a database of shapes 101 based on the difficulty level and/or on the similarity metrics.

In the example of FIG. 14, the at least one second shape 101 is selected based on the difficulty level. However, said second shape may be selected based on the similarity metrics. In this case, the reception S60 of the difficulty level is optional.

In one embodiment, a plurality of predefined shapes 101 is displayed, each shape 101 of the plurality being displayed at the end of a time interval, in order to provide repetitive or cyclic rehabilitation exercises.

In one embodiment, the time interval is a fixed time interval.

In one embodiment, the time interval is selected based on the similarity metrics. For instance, the $N^{th}$ shape of the plurality of predefined shapes may be displayed when the similarity metrics related to the $N^{th-1}$ shape is above a predefined threshold.

As can be seen in FIG. 14, the method may further comprise a step of rotating S71 the interactive screen by an angle comprised between 0° and 90°. In this embodiment, the method comprises:
  f.3) receiving S60 as input a difficulty level;
  f.4) rotating S71 the device 10 by an angle, said angle of rotation being calculated S62 based on the difficulty level.

This embodiment advantageously allows to increase or decrease the difficulty level of the rehabilitation exercises. This embodiment further allows to provoke desired rehabilitation movements such as wrist extension and wrist flexion, by increasing the rotation angle. On a horizontal surface, the subject would not be incited to perform such movements.

In a preferred embodiment, the difficulty level is selected by the therapist. For example, the therapist may choose, if the subject is too weak, to decrease the difficulty level, hence the rotation angle.

In another embodiment, the difficulty level, and subsequently the angle of rotation, may be automatically increased or decreased depending on a predefined parameter. For instance, the difficulty level may be selected depending on the subject performances as measured by the similarity metrics.

The displaying step S70 and the rotation step S71 may be performed in combination (as can be seen FIG. 14) or in alternative (i.e., only the left branch or the right branch of the flow chart depicted in FIG. 14 is performed).

In one embodiment, the at least one predefined shape is provided in a videogame environment, so that the bimanual rehabilitation exercises on the rotating screen are performed in the context of games, such as for example climbing simulations.

In one embodiment, the steps S20 to S70 or S20 to S71 of the method are periodically repeated at a predefined repetition frequency.

In one embodiment, the repetition frequency is calculated by the processing unit, based on the difficulty level selected by the therapist.

In one embodiment, the repetition frequency is superior to 500 times/hours, preferably superior to 1000 times/hours. This ensures that the repetition frequency is high enough to provide an intensive rehabilitation.

In this embodiment, the same predefined shape or different predefined shapes may be displayed at the repetition frequency. Said shapes may be provided in a videogame environment, so that the bimanual rehabilitation exercises are performed in the context of games such as hitting-the-target games.

Figure 15:
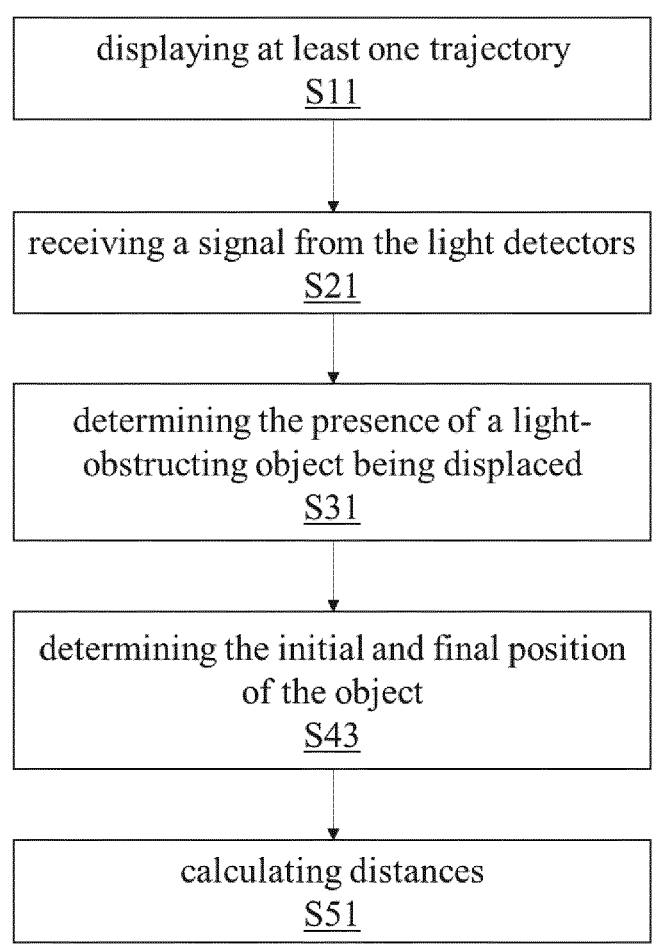
FIG. 15 is a flow chart illustrating an exemplary method for assessment of the upper limbs compliant with the disclosure in which a trajectory 103 is displayed.

FIG. 15 illustrates the main steps of a method compliant with the present disclosure, which comprises:
- displaying S11 on an interactive screen equipped with an array of light emitters and an array of light detectors as previously described at least one target trajectory 103 comprising a starting point, an end point and, optionally, a line connecting the starting point and the end point;
- receiving S21 as input the signal generated from the light detectors;
- based on the received signal, determining 31 the presence of an object 30 obstructing at least one light beam on the detection surface 110;
- if the presence of an object 30 being displaced on the interactive screen is determined, determine S43 the position of the object 30, so as to obtain an object trajectory comprising an initial object position and a final object position;
- calculating S51 a first distance between the initial object position and the starting point of the target trajectory 103, and a second distance between the final object position and the end point of the target trajectory 103;
- optionally, displaying a feedback based on the first and/or the second distance.

In this embodiment, the feedback relates to the initial object position and/or the final object position of an object 30 moved on the interactive screen, hence it does not relate to the path traveled by the object. This embodiment is particularly advantageous to provide upper limb rehabilitation exercises for training the subject's pointing accuracy.

In one embodiment, the target trajectory 103 may be a graphical element, such as a railway, a street or a maze, of a videogame displayed on the interactive screen, so that the bimanual rehabilitation exercises are performed in a ludic context.

In the example illustrated in FIG. 15, the initial object position and the final object position of the object trajectory are determined during step S43.

However, in some examples, the intermediate positions of said object trajectory may also be determined. In this case, the method may further comprise the following steps:
- at regular time intervals, based on the received signal, determining the position of an object 30 displaced on an interactive screen as previously described, so as to obtain an object trajectory comprising an initial object position, a plurality of intermediate object positions and a final object position;
- for each intermediate object position of the plurality, calculating S51 the distance between the intermediate object position and the target trajectory 103;
- displaying on the interactive screen a feedback based on the calculated distance.

By the distance between the object position and the target trajectory 103 it is meant the length of the line segment which joins the object position to nearest point on the target trajectory.

The target trajectory 103 may be a curved line, a straight line or a combination thereof.

This method allows to provide a bimanual rehabilitation task consisting in moving an object 30 on an interactive screen while reproducing a target trajectory 103 displayed on said screen, the calculated distance allows to assess the subject performing the task.

The feedback related to the distance between each intermediate object position and the target trajectory 103 allows to provide information about the displacement of the object 30 moved on the interactive screen, and about its deviation from the target trajectory 103.

In one embodiment, the feedback based on the calculated distance is displayed in real-time during the whole exercise duration, i.e., after each distance calculation, until the object 30 reaches the final object position. This embodiment allows to inform the subject in real-time about his performance, thereby allowing him to correct the object 30 movement accordingly.

In one embodiment, the feedback related to the intermediate object positions is displayed when the object 30 reaches the final object position, i.e., at the end of the rehabilitation exercise. The feedback is displayed when the object 30 reaches the final object position may be a function of all the distances calculated for each intermediate object position, such as for example the average distance.

In one embodiment, both feedbacks related to the intermediate object positions and feedbacks related to the initial and final object positions are displayed.

The displayed feedbacks may be a visual feedback or audio-visual signals.

In one embodiment, the method according to the present invention further comprises generating, by a processing unit, a report. In one embodiment, the method further comprises displaying the generated report. The report may comprise data related to the tasks performed by the subject, such as the similarity metrics and the calculated distances as defined hereabove. The report provides a quantitative and objective assessment of the subject's upper limbs and/or the subject progression after one or more rehabilitation sessions. The data in the report may be displayed as line charts, bar graphs, scatterplot charts, pie charts, area charts, histograms, spider charts, heat maps or a combination thereof.

In one embodiment, the present device comprises a therapist-side GUI that allows the therapist to visualize information for assessing the subject's upper limbs, such as the feedbacks, the similarity metrics, the report.

According to one embodiment, the predefined shapes 101, the predefined properties 102 and the target trajectories 103 as described hereabove are provided in a videogame scenario, so as to ensure the immersion of the subject in the rehabilitation session.

Moreover, in the present invention the immersion of the subject in the rehabilitation session is further increased by using game scenarios that simulate real-life situations and/or by using everyday objects. For instance, a rotation of the interactive screen 10 may be provided in the context of a climbing game. For instance, fixed predefined shapes may be provided in the context of a city building game whereas different shapes 101 displayed at different instant of times may be provided in the context of a hitting-the target game.

In one embodiment, the present device comprises a therapist-side GUI that allows the therapist to select a videogame among a list of therapeutic videogames.

Advantageously, the high level of immersion ensured by the present invention allows to provide an intensive functional rehabilitation of the upper limbs.

In one embodiment, the present invention provides a device and a method for intensive functional rehabilitation of the upper limbs for children and adults suffering from motor impairments, and especially for brain-damaged patients. In some examples, the device is used for assessment of the upper limbs in non-medical contexts, such as for instance for pediatric (or child development) monitoring and research, sport, education, and the like.

In one embodiment, interactive screen and device 10 have the same meaning.

The present invention also relates to a computer program product for bimanual rehabilitation of a subject, the computer program product comprising instructions which, when the program is executed by a computer, cause the computer to carry out the steps of the method described hereabove.

The computer program product to perform the method as described above may be written as computer programs, code segments, instructions or any combination thereof, for individually or collectively instructing or configuring the processor or computer to operate as a machine or special-purpose computer to perform the operations performed by hardware components. In one example, the computer program product includes machine code that is directly executed by a processor or a computer, such as machine code produced by a compiler. In another example, the computer program product includes higher-level code that is executed by a processor or a computer using an interpreter. Programmers of ordinary skill in the art can readily write the instructions or software based on the block diagrams and the flow charts illustrated in the drawings and the corresponding descriptions in the specification, which disclose algorithms for performing the operations of the method as described above.

The present invention also relates to a computer-readable storage medium comprising instructions which, when the program is executed by a computer, cause the computer to carry out the steps of the method according to any one of the embodiments described hereabove.

According to one embodiment, the computer-readable storage medium is a non-transitory computer-readable storage medium.

Computer programs implementing the method of the present embodiments can commonly be distributed to users on a distribution computer-readable storage medium such as, but not limited to, an SD card, an external storage device, a microchip, a flash memory device, a portable hard drive and software websites. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While various embodiments have been described and illustrated, the detailed description is not to be construed as being limited hereto. Various modifications can be made to the embodiments by those skilled in the art without departing from the true spirit and scope of the disclosure as defined by the claims.

The invention claimed is:

1. A device for assessing and/or rehabilitating the upper limbs of a subject, said device comprising a display surface, a detection surface, and a processing unit, wherein:
    the display surface is configured to display at least one predefined shape having a predefined position and a predefined orientation with respect to the display surface;
    the detection surface comprises an array of light emitters arranged to generate a grid of light beams on the display surface, and an array of light detectors, each light detector being configured to detect the light beam from a respective light emitter and to generate a signal representative of the detected light; and
    the processing unit is configured to:
        receive as input the signal generated from the light detectors;

based on the received signal, determine the presence of an object obstructing at least one light beam on the detection surface;

if the presence of an object is determined, determine the position, the orientation and the shape of the object;

calculate a similarity metrics based on at least one of the predefined positions, orientation and shape of the shape displayed on the display surface and respectively at least one of the previously determined position, orientation and shape of the object.

2. A system for assessing and/or rehabilitating the upper limbs of a subject, the system comprising the device according to claim 1 and at least one object, the object comprising an object support, the device-side of the object support comprising supporting legs being a pattern of obstacles configured to minimize the obstruction of the light beams of the grid, and wherein the processing unit is further configured to:

receive as input a library of patterns wherein each pattern is associated with at least one object property;

based on the signal generated from the light detectors, determine the presence of a pattern of obstacles of an object support on the detection surface;

-if the pattern of obstacles matches a pattern in the library, determine a property of the object, said property of the object being the at least one object property associated with the matching pattern in the library.

3. The system according to claim 2, wherein the display surface is configured to display at least one predefined property that does not affect the light beam obstruction, and the processing unit is further configured to:

calculate a similarity metrics based on the determined property of the object, and the predefined property.

4. The system according to claim 3, wherein the object property is the object color, the object weight, the object temperature, the object texture, or the object material.

5. The system according to claim 3, wherein the processing unit is configured to detect at least 5 patterns of obstacles simultaneously.

6. The system according to claim 2, wherein the object property is the object color, the object weight, the object temperature, the object texture, or the object material.

7. The system according to claim 6, wherein the processing unit is configured to detect at least 5 patterns of obstacles simultaneously.

8. The system according to claim 2, wherein the processing unit is configured to detect at least 5 patterns of obstacles simultaneously.

9. An apparatus comprising the system according to claim 2, wherein the device is installed on the table top of a table, said table comprising elements for rotating the table top about a horizontal axis of an angle comprised between 0° and 90°.

10. The apparatus of claim 9 wherein the apparatus further comprises a lifting device for lifting and lowering the device.

11. The apparatus of claim 9 wherein the table further comprises at least two pairs of casters.

12. The apparatus of claim 9 wherein the table further comprises loudspeakers.

13. The system according to claim 2, wherein at least one of the objects is selected among everyday objects.

14. The system according to claim 2, wherein the object support which is reversibly attached to the display surface.

15. The system according to claim 2, wherein the processing unit is further configured to:

display on the display surface of the device at least one target trajectory comprising a starting point and an end point;

receive as input the signal generated from the light detectors;

based on the received signal, determine the presence of an object obstructing at least one light beam on the detection surface;

if the presence of an object is determined, determine the position of the object, so as to obtain an object trajectory comprising an initial object position and a final object position;

calculate a first distance between the initial object position and the starting point of the target trajectory, and a second distance between the final object position and the end point of the target trajectory.

16. The system according to claim 2, wherein the predefined shapes, the predefined properties and the target trajectories are provided in a videogame scenario.

17. The device according to claim 1, wherein the device is configured to be connected via a wired or wireless network to a peripheral device.

18. The device according to claim 1, wherein the light emitters are infrared LEDs.

19. The device according to claim 1, wherein the display surface is further configured to display feedback.

20. The device according to claim 1, wherein the device further comprises a memory configured to store data relative to the assess and/or the rehabilitation.

* * * * *